US010531907B2

(12) United States Patent
Sharp et al.

(10) Patent No.: US 10,531,907 B2
(45) Date of Patent: Jan. 14, 2020

(54) DEVICES, SYSTEMS, AND METHODS FOR TREATING ULCERATIVE COLITIS AND OTHER INFLAMMATORY BOWEL DISEASES

(71) Applicant: COVIDIEN LP, Mansfield, MA (US)

(72) Inventors: Robert M. Sharp, Boulder, CO (US); Darion R. Peterson, Longmont, CO (US); Duane E. Kerr, Loveland, CO (US); Arlen K. Ward, Thornton, CO (US); Anthony B. Ross, Boulder, CO (US); Rebecca J. Coulson, Lyons, CO (US); William H. Nau, Jr., Longmont, CO (US)

(73) Assignee: Covidien LP, Mansfield, MA (US)

( * ) Notice: Subject to any disclaimer, the term of this patent is extended or adjusted under 35 U.S.C. 154(b) by 442 days.

(21) Appl. No.: 15/340,553

(22) Filed: Nov. 1, 2016

(65) Prior Publication Data

US 2017/0143400 A1    May 25, 2017

Related U.S. Application Data

(60) Provisional application No. 62/258,053, filed on Nov. 20, 2015.

(51) Int. Cl.
*A61B 18/04* (2006.01)
*A61M 37/00* (2006.01)
*A61B 18/00* (2006.01)

(52) U.S. Cl.
CPC .............. *A61B 18/04* (2013.01); *A61M 37/00* (2013.01); *A61B 2018/00494* (2013.01); *A61B 2018/046* (2013.01)

(58) Field of Classification Search
CPC ................ A61B 2018/00011; A61B 2018/00273; A61B 2018/00279; A61B 2018/00285;

(Continued)

(56) References Cited

U.S. PATENT DOCUMENTS 3,779,882 A    12/1973  Rosenthal
4,911,163 A *  3/1990   Fina ................. A61B 17/22032
                                               604/101.04

(Continued)

FOREIGN PATENT DOCUMENTS

WO    2004/088233 A2    10/2004
WO    2013/086461 A1    6/2013

OTHER PUBLICATIONS

Notification of Transmittal of the International Search Report and the Written Opinion of the International Search Authority, or the Declaration issued in corresponding application No. PCT/US2016/060623 dated Mar. 7, 2017.

*Primary Examiner* — Ronald Hupczey, Jr.
(74) *Attorney, Agent, or Firm* — Carter, DeLuca & Farrell LLP

(57) ABSTRACT

A method of treating bowel diseases includes introducing a fluid into a portion of a patient's colon and applying energy thereto from an external energy source such that the fluid and the energy cooperate to treat tissue of the portion of the patient's colon in contact with the fluid. Another method of treating inflammatory bowel diseases includes sealing a portion of a patient's colon, introducing an electrically-conductive fluid thereto, and energizing an electrode disposed therein to treat tissue of the portion of the patient's colon in contact with the electrically-conductive fluid. Another method of treating inflammatory bowel diseases includes sealing a portion of a patient's colon and introducing a heated fluid at a temperature equal to or above 60° C. to treat tissue of the portion of the patient's colon in contact with the heated fluid.

11 Claims, 6 Drawing Sheets

(58) Field of Classification Search
CPC .... A61B 2018/00482; A61B 2018/046; A61B 2018/1253
See application file for complete search history.

(56) References Cited

U.S. PATENT DOCUMENTS

| | | | |
|---|---|---|---|
| 5,693,044 A | 12/1997 | Cosmescu | |
| 6,136,021 A | 10/2000 | Tockman et al. | |
| 6,139,571 A | 10/2000 | Fuller et al. | |
| 6,192,279 B1 | 2/2001 | Barreras, Sr. et al. | |
| RE37,704 E | 5/2002 | Eshel | |
| 6,419,673 B1 * | 7/2002 | Edwards | A61B 18/1477 606/41 |
| 6,551,311 B2 | 4/2003 | Lee et al. | |
| 6,620,159 B2 | 9/2003 | Hegde | |
| 6,638,273 B1 | 10/2003 | Farley et al. | |
| 6,697,676 B2 | 2/2004 | Dahl et al. | |
| 6,758,857 B2 | 7/2004 | Cioanta et al. | |
| 6,802,841 B2 * | 10/2004 | Utley | A61B 18/1206 128/898 |
| 7,150,745 B2 | 12/2006 | Stern et al. | |
| 7,278,991 B2 | 10/2007 | Morris et al. | |
| 7,326,201 B2 | 2/2008 | Fjield et al. | |
| 7,630,769 B2 | 12/2009 | Knudson et al. | |
| 7,693,577 B2 | 4/2010 | Knudson et al. | |
| 8,667,674 B2 | 3/2014 | Buysse | |
| 8,915,867 B2 | 12/2014 | Imran et al. | |
| 8,992,518 B2 | 3/2015 | Fridman et al. | |
| 9,039,703 B2 | 5/2015 | Karwei | |
| 9,078,655 B2 | 7/2015 | Manwaring et al. | |
| 9,138,251 B2 | 9/2015 | Kuehner et al. | |
| 9,216,280 B1 | 12/2015 | Hakki et al. | |
| 9,265,556 B2 | 2/2016 | Manwaring et al. | |
| 9,474,482 B2 | 10/2016 | Devanaboyina | |
| 2002/0049438 A1 | 4/2002 | Sharkey et al. | |
| 2003/0040785 A1 | 2/2003 | Maschino et al. | |
| 2004/0215296 A1 | 10/2004 | Ganz et al. | |
| 2007/0043350 A1 | 2/2007 | Soltesz et al. | |
| 2007/0173798 A1 * | 7/2007 | Adams | A61B 18/04 606/27 |
| 2007/0203486 A1 | 8/2007 | Young | |
| 2010/0094270 A1 | 4/2010 | Sharma | |
| 2011/0213353 A1 | 9/2011 | Lee et al. | |
| 2013/0165924 A1 | 6/2013 | Mathur et al. | |
| 2013/0172877 A1 | 7/2013 | Subramaniam et al. | |
| 2014/0277420 A1 | 9/2014 | Migliazza et al. | |
| 2015/0112323 A1 | 4/2015 | Hagg | |
| 2015/0119867 A1 | 4/2015 | Barman et al. | |
| 2015/0126990 A1 * | 5/2015 | Sharma | A61B 5/6853 606/30 |
| 2015/0148738 A1 | 5/2015 | Caplan et al. | |

* cited by examiner

DEVICES, SYSTEMS, AND METHODS FOR TREATING ULCERATIVE COLITIS AND OTHER INFLAMMATORY BOWEL DISEASES

CROSS REFERENCE TO RELATED APPLICATION

The present application claims the benefit of and priority to U.S. Provisional Application Ser. No. 62/258,053, filed on Nov. 20, 2015, the entire contents of which are incorporated herein by reference.

BACKGROUND

Technical Field

The present disclosure relates to treatment of Inflammatory Bowel Diseases (IBDs) and, more particularly, to surgical devices, systems, and methods for treating ulcerative colitis and other IBDs, e.g., Crohn's Disease.

Background of Related Art

Ulcerative colitis, an IBD, is a disease of the colon in which inflammation and ulcers, or sores, form on the interior wall of the colon. Ulcerative colitis manifests itself, usually intermittently and at varying degrees of severity, in symptoms such as stomach pain, diarrhea, and/or bloody stool. Typically, anti-inflammatory medication(s) are prescribed for patients suffering from ulcerative colitis. In extreme cases, chronic cases, or cases in which medication(s) fails to adequately treat the patient's symptoms, surgery to remove all or part of the diseased portions of the rectum and/or colon may be performed.

Although medication(s) and surgical removal of diseased portions of the rectum and/or colon are effective in certain instances, there is a need for surgical devices, systems, and methods to more effectively and/or efficiently treat ulcerative colitis and other IBDs, e.g., Crohn's Disease, while minimizing side effects and damage to un-diseased tissue.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

A method of treating bowel diseases provided in accordance with the present disclosure includes introducing a fluid into a portion of a patient's colon and applying energy towards the portion of the patient's colon from an energy source positioned externally of the patient such that the fluid and the energy cooperate to treat tissue of the portion of the patient's colon in contact with the fluid.

In aspects of the present disclosure, introducing the fluid includes at least partially filling the portion of the patient's colon with the fluid. At least partially filling the portion of the patient's colon may include sealing off an area of the patient's colon to retain the fluid therein. Sealing off the area may include clamping the area on at least one end thereof or plugging the area on at least one end thereof.

In aspects of the present disclosure, the energy source is a microwave energy source and wherein the fluid defines a dielectric constant greater than a dielectric constant of tissue such that, upon application of microwave energy from the microwave energy source, the fluid is heated, thereby treating tissue of the portion of the patient's colon in contact with the fluid. Alternatively, the energy source may be an ultrasound energy source and an acoustic impedance difference between the fluid and tissue may be utilized such that, upon application of ultrasonic energy from the ultrasound energy source, heating occurs at an interface between the fluid and tissue, thereby treating tissue of the portion of the patient's colon in contact with the fluid.

Another method of treating bowel diseases provided in accordance with the present disclosure includes sealing off a portion of a patient's colon, introducing an electrically-conductive fluid into the sealed off portion of the patient's colon, and energizing an electrode disposed within the portion of the patient's colon such that energy is conducted through the electrically-conductive fluid and tissue of the portion of the patient's colon in contact with the electrically-conductive fluid to treat tissue of the portion of the patient's colon in contact with the electrically-conductive fluid.

In an aspect of the present disclosure, the electrically-conductive fluid is an electrically-conductive gel, argon plasma, or isotonic saline.

In another aspect of the present disclosure, the electrically-conductive fluid includes at least one medicament therein to facilitate healing of treated tissue.

In yet another aspect of the present disclosure, sealing off the portion of the patient's colon includes clamping or plugging at least one end of the portion of the patient's colon. In such aspects, the method may further include inserting the electrode through a clamped or plugged end of the portion of the patient's colon and into the portion of the patient's colon prior to energizing the electrode.

In still another aspect of the present disclosure, sealing off the portion of the patient's colon includes introducing an end effector into the patient's colon and engaging first and second sealing members of the end effector with respective ends of the portion of the patient's colon. In such aspects, introducing the electrically-conductive fluid may include pumping the electrically-conductive fluid through a port of the end effector disposed between the first and second sealing members, and/or energizing the electrode may include energizing an electrode of the end effector disposed between the first and second sealing members.

In still yet another aspect of the present disclosure, energizing the electrode includes applying monopolar energy to the electrode.

Another method of treating bowel diseases provided in accordance with the present disclosure includes sealing off a portion of a patient's colon and introducing a heated fluid at a temperature equal to or above 60° C. into the sealed off portion of the patient's colon to treat tissue of the portion of the patient's colon in contact with the heated fluid.

In aspects of the present disclosure, sealing off the portion of the patient's colon includes clamping or plugging at least one end of the portion of the patient's colon. In such aspects, introducing the heated fluid may include inserting a probe through a clamped or plugged end of the portion of the patient's colon and pumping the heated fluid into the sealed off portion of the patient's colon through a port of the probe disposed within the sealed off portion of the patient's colon.

In aspects of the present disclosure, sealing off the portion of the patient's colon includes introducing an end effector into the patient's colon and engaging first and second sealing members of the end effector with respective ends of the portion of the patient's colon. In such aspects, introducing the heated fluid may include pumping the heated fluid into the sealed off portion of the patient's colon through a port of the end effector disposed between the first and second sealing members.

BRIEF DESCRIPTION OF THE DRAWINGS

Various aspects and features of the present disclosure described herein with reference to the drawings wherein.

DETAILED DESCRIPTION

As IBD's such as ulcerative colitis may only affect portions of the colon, it is desirable to focus treatment towards such diseased areas while limiting damage to surrounding tissue and critical structures. Accordingly, the present disclosure provides various devices, systems, and methods configured to facilitate the focused or controlled treatment of diseased portions of the colon while limiting damage to surrounding portions of the colon and other surrounding tissue and critical structures.

Figure 1:
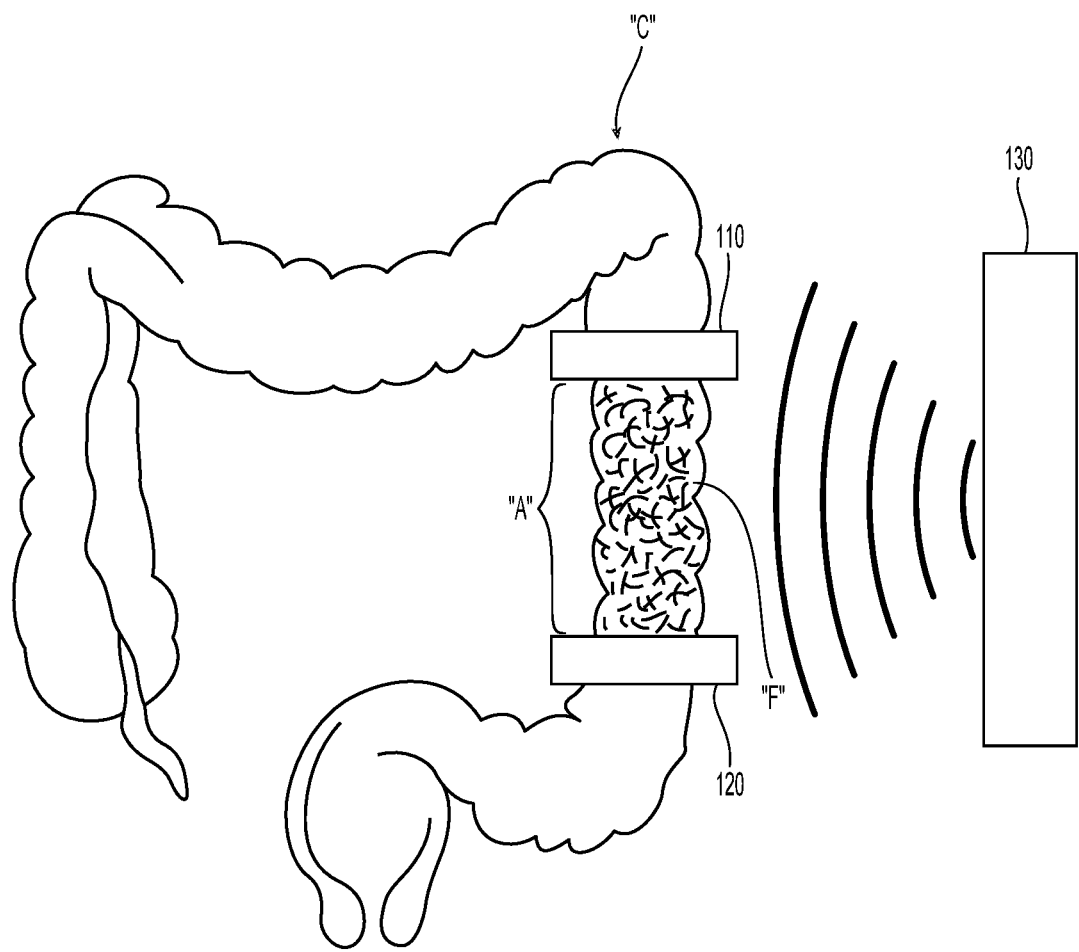
FIG. 1 is a schematic illustration of a method provided in accordance with the present disclosure for use in treating a diseased portion of the colon.

Turning now to FIG. 1, in embodiments provided in accordance with the present disclosure, in order to treat a diseased area "A" of the colon "C," the diseased area "A" is initially filled with a fluid "F" and thereafter sealed off to retain the fluid "F" within the diseased area "A." This may be accomplished by clamping off a first end of the diseased area "A" with a first clamping member 110, filling the diseased areas "A" with the fluid "F" through the open second end thereof, and thereafter clamping off the second end with a second clamping member 120. Clamping members 110, 120 may be occluding clips, constricting bands, forceps jaws, a combination thereof, or any other clamping members 110, 120 suitable for sealing off the first and second ends of the diseased area "A" of the colon "C" so as to retain the fluid "F" therein. As an alternative to clamping members 110, 120, plugs, e.g., similar to plugs 310, 320 (FIG. 3), or other suitable structures for sealing off diseased area "A" may also be utilized.

With the diseased area "A" filled with the fluid "F" and sealed off so as to retain the fluid "F" therein, a microwave source 130, disposed externally of the patient, may be energized to direct microwave energy towards the diseased area "A." The fluid "F" may be water, or other suitable bio-compatible fluid having a dielectric constant greater than tissue and critical structures. Water is advantageous in that it is obviously bio-compatible and has a high dielectric constant. More specifically, the molecular makeup of water facilitates the absorption of microwave energy which ultimately leads to the rapid heating of water in the presence of microwave energy as compared to other matter such as tissue and critical structures, which necessarily have a lower water content than water itself.

Upon application of the microwave energy from microwave source 130, the fluid "F," e.g., water, within the diseased area "A" is heated rapidly, faster than any surrounding tissue and critical structures, which have lower dielectric constants than water. The microwave energy is applied so as to heat the water sufficiently such that the layer of inflamed, diseased tissue defining the diseased area "A" of the colon "C" is thermally treated. Such thermal treatment may include burning, charring, ablating, coagulating, and/or desiccating the inflamed layer of tissue. By thermally treating the diseased area "A" in this manner and thereafter allowing the tissue to heal, the inflammation and ulceration can be reduced or eliminated entirely, thereby reducing the associated pain and discomfort. The particular fluid "F" provided and selective control of the frequency and power settings of the microwave source 130 may be utilized to ensure sufficient heating of the fluid "F" while inhibiting damage to surrounding tissue and critical structures.

As an alternative to filling the diseased area "A" with fluid "F" and sealing off the diseased area "A," the fluid "F" may be sprayed, coated, or otherwise applied to the diseased area "A." Further still, rather than sealing off diseased area "A," the entire colon "C" may be filled with the fluid "F" or sprayed, coated, etc. therewith. In either configuration, similarly as above, upon application of the microwave energy from the microwave source 130, the fluid "F," e.g., water, is heated so as to thermally treat the diseased area "A" of the colon "C" while inhibiting damage to surrounding tissue and critical structures.

Figure 2:
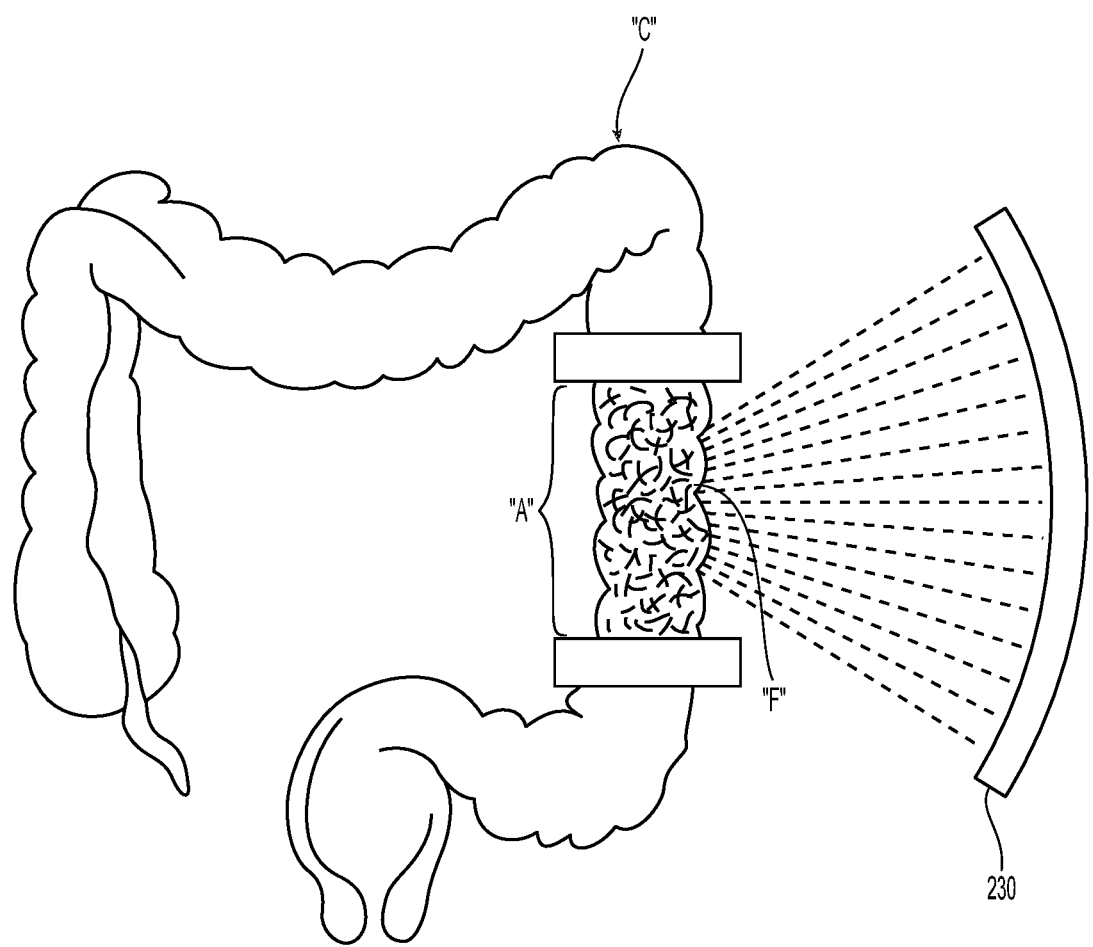
FIG. 2 is a schematic illustration of another method provided in accordance with the present disclosure for use in treating a diseased portion of the colon.

Turning now to FIG. 2, in some embodiments, rather than utilizing microwave energy, an ultrasound source 230, positioned externally of the patient, may be utilized to direct focused ultrasonic energy to the diseased area "A" of the colon "C." In such configurations, the fluid "F" may be air, or other suitable bio-compatible fluid that has a sufficiently different acoustic impedance as compared to tissue, e.g., the layer of inflamed, diseased tissue defining the diseased area "A" of the colon "C." Such a fluid "F" establishes an impedance mismatch at the interface of the fluid "F" with the layer of inflamed, diseased tissue defining the diseased area "A."

In use, upon application of focused ultrasonic energy from the ultrasound source 230 to the diseased area "A," localized heating of tissue occurs at the impedance mismatch interface, e.g., the interface between the fluid "F" and the layer of inflamed, diseased tissue defining the diseased area "A," as the ultrasonic energy is transmitted from the tissue to the fluid "F" and vice versa. This localized heating is used to thermally treat the layer of inflamed, diseased tissue defining the diseased area "A" of the colon "C," e.g., via burning, charring, ablating, coagulating, and/or desiccating the tissue. The particular fluid "F" provided and selective control of the frequency and power settings of the ultrasound source 130 may be utilized to ensure sufficient heating at the interface so as to effectively treat tissue while inhibiting damage to surrounding tissue and critical structures.

Figure 3:
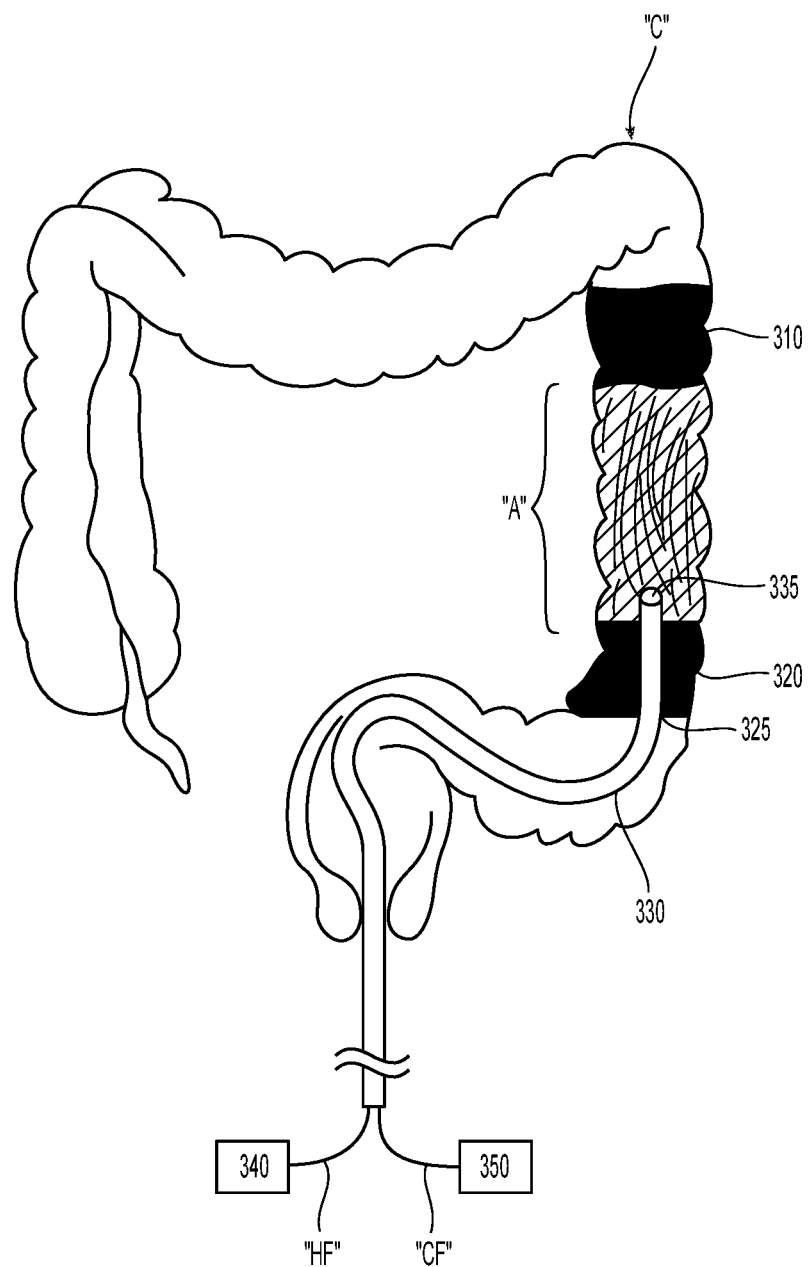
FIG. 3 is a schematic illustration of yet another method provided in accordance with the present disclosure for use in treating a diseased portion of the colon.

Referring to FIG. 3, in some embodiments, the diseased area "A" of the colon "C" may be sealed off using first and second plugs 310, 320 disposed at either end of the diseased area "A." Plugs 310, 320 may be resiliently flexible plugs 310, 320 configured to conform to the internal diameter of the colon "C" at each end of the diseased area "A" to sealingly enclose the diseased area "A," or any other suitable plugs configured to seal off the diseased area "A." Alternatively, clamping members, e.g., clamping members 110, 120 (FIG. 1), may be utilized for similar purposes.

One of the plugs, e.g., plug 320, may include a zero-closure valve 325 defined therethrough. Zero-closure valve 325 may be a slit-valve, a duckbill valve, or any other suitable valve that is biased towards a closed position to inhibit the passage of fluid therethrough and is capable of sealingly receiving an instrument therethrough.

With continued reference to FIG. 3, in use, initially, plugs 310, 320 are positioned within the colon "C" to sealingly enclose the diseased area "A" to be treated. Thereafter, a probe 330 is inserted through the zero-closure valve 325 and into the diseased area "A." Probe 330 may include one or more ports 335 defined about the radial outer peripheral surface of probe 330 and/or at the distal end of probe 330. Probe 330 is inserted through zero-closure valve 325 and into the diseased area "A" such that each of the ports 335 thereof is disposed within the diseased area "A." Probe 330 may be inserted through the anus and navigated through the colon "C" to the diseased area "A," as illustrated, although other approaches are also contemplated. Further, probe 330 is sufficiently insulated such that the exterior thereof remains at or near ambient temperature, thus inhibiting inadvertent damage to tissue and/or harm to the operator, the importance of which will be realized below.

Once probe 330 is positioned as detailed above, a heated fluid "HF," e.g., hot air, hot water, etc., from a heated fluid source 340 is pumped through probe 330, out ports 335, and into the diseased area "A." The heated fluid "HF" is pumped into the diseased area "A" so as to at least partially fill the diseased area "A" and contact the layer of inflamed, diseased tissue defining the diseased area "A" of the colon "C." The heated fluid "HF" may be heated to or above 43° C. or, in some embodiments, to or above about 60° C., such that the heated fluid "HF" is capable of thermally treating the layer of inflamed, diseased tissue, e.g., via burning, charring, ablating, coagulating, and/or desiccating the inflamed layer of tissue.

Once sufficient thermal treatment of the inflamed, diseased layer of tissue with the heated fluid "HF" has been achieved, the heated fluid source 340 may be transitioned from a pumping or pressure mode to a suction mode to withdraw the heated fluid "HF" from the diseased area "A." Thereafter or concurrently therewith, a cooling fluid source 350 may be activated to pump cooling fluid "CF," e.g., ice water, cold air, etc. through probe 330, out ports 335, and into the diseased area "A" to cool the treated tissue. The temperature and duration of application of the heated fluid "HF" and/or cooling fluid "CF" can be controlled such that thermal treatment extends sufficiently deep into the layer of inflamed, diseased tissue so as to adequately treat the diseased tissue, while being sufficiently contained so as to inhibit damage to surrounding tissue and critical structures.

Figure 4A:
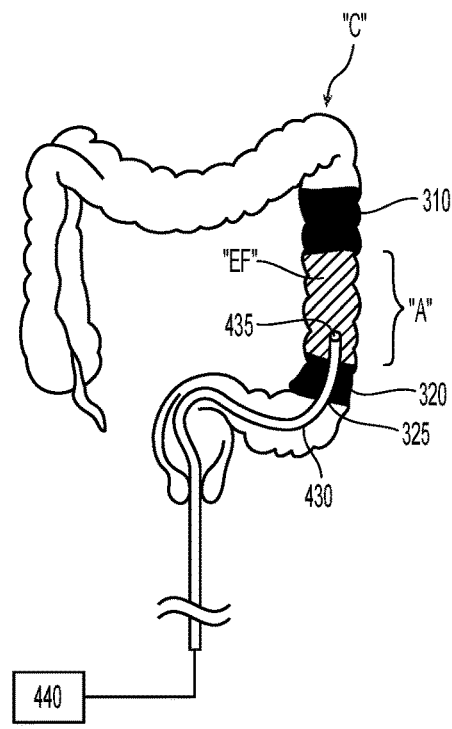
FIGS. 4A-4B are schematic illustrations of still another method provided in accordance with the present disclosure for use in treating a diseased portion of the colon.
Figure 4B:
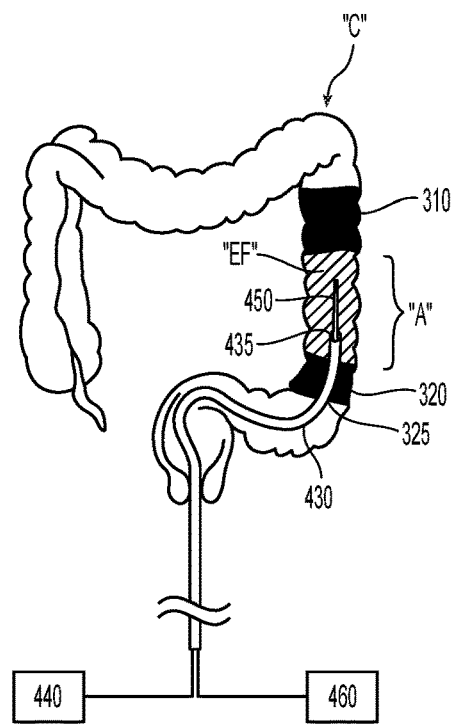

Turning to FIGS. 4A and 4B, in some embodiments, the diseased area "A" of the colon "C" may be sealed off using plugs 310, 320, similarly as detailed above with respect to FIG. 3. Thereafter, a probe 430 is inserted through the zero-closure valve 325 of plug 320 and into the diseased area "A." Probe 430 may include one or more ports 435, similarly as detailed above with respect to probe 330 (FIG. 3). Probe 430 is inserted into the diseased area "A" such that each of the ports 435 thereof is disposed within the diseased area "A."

Once probe 430 is positioned as detailed above, an electrically-conductive fluid "EF" from a fluid source 440 is pumped through probe 430, out ports 435, and into the diseased area "A." The electrically-conductive fluid "EF" is pumped into the diseased area "A" so as to at least partially fill the diseased area "A" and contact the layer of inflamed, diseased tissue defining the diseased area "A" of the colon "C." The electrically-conductive fluid "EF" may be any suitable bio-compatible fluid capable of conducting electrical energy therethrough such as, for example, a conductive gel, isotonic saline, argon plasma, etc. A conductive gel utilized as the electrically-conductive fluid "EF," for example, may further be configured as a bio-absorbable gel configured for absorption into surrounding tissue and/or may include medicament, e.g., a debridement agent, an antimicrobial agent, an antibiotic, a growth factor, an analgesic, etc., to promote healing of tissue after treatment thereof.

Probe 430 is further configured to receive one or more electrodes 450 therethrough, e.g., via the same or different lumen and/or port 435 than those that provide the electrically-conductive fluid "EF." More specifically, once the electrically-conductive fluid "EF" has been pumped into the diseased area "A," the fluid source 440 may be deactivated and one or more electrodes 450 inserted through or advanced from probe 430 such that each of the electrodes 450 protrudes distally from probe 430 into the electrically-conductive fluid "EF" disposed within the diseased area "A."

An electrosurgical generator 460 coupled to each of the electrodes 450 may then be activated to supply electrosurgical energy to the electrodes 450. Generator 460 may be configured to supply monopolar energy to a single electrode 450 (wherein energy is returned via a remote return pad (not shown) placed on the patient), or may be configured to supply bipolar energy to multiple electrodes 450 (wherein at least one electrode 450 is charged to a positive potential and at least another electrode 450 is charged to a negative potential). Regardless of whether monopolar or bipolar energy is utilized, the electrically-conductive fluid "EF" facilitates the conduction of energy through the layer of inflamed, diseased tissue defining the diseased area "A" of the colon "C" for electrosurgically treating the layer of inflamed, diseased tissue, e.g., via burning, charring, ablating, coagulating, and/or desiccating the inflamed layer of tissue.

Once tissue is sufficiently treated, the generator 460 may be deactivated, the electrode(s) 450 removed, and the electrically-conductive fluid "EF" withdrawn from the diseased area "A." In order to withdraw the electrically-conductive fluid "EF," the fluid source 440 is operated in a suction mode. Alternatively, in embodiments where an absorbable fluid and/or a fluid containing medicaments is provided, the electrically-conductive fluid "EF" may be left behind (permanently or for a period of time) to be absorbed into the body and/or facilitate healing of the treated tissue.

Figure 5A:
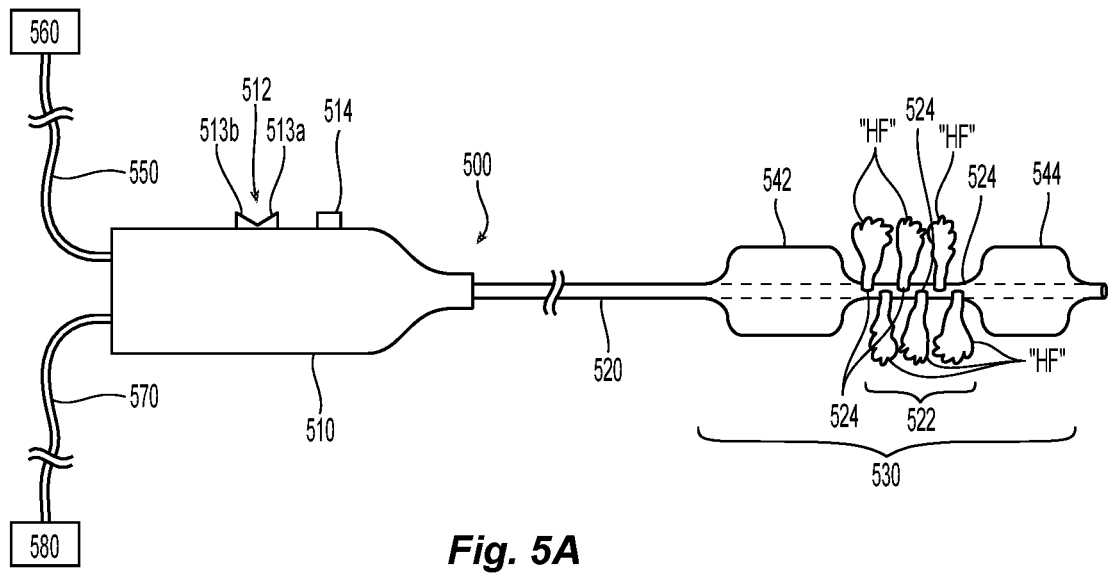
FIG. 5A is a side view of a device provided in accordance with the present disclosure configured for use in treating a diseased portion of the colon.
Figure 5B:
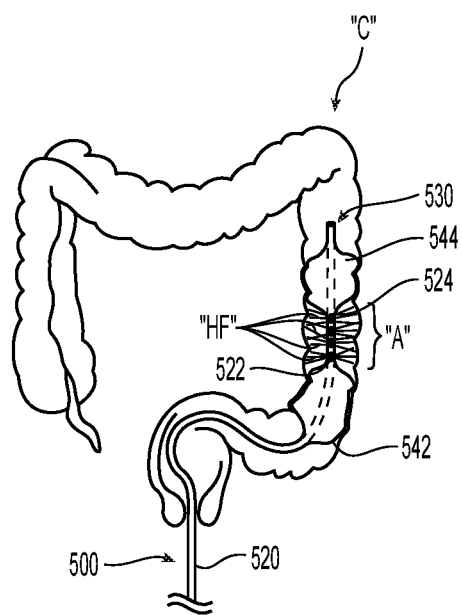
FIG. 5B is a schematic illustration of the device of FIG. 5A shown in use treating a diseased portion of the colon.

Referring to FIGS. 5A and 5B, an instrument 500 provided in accordance with the present disclosure and configured for use in treating IBD's is shown generally including a handle 510, a shaft 520 extending distally from handle 510, and an end effector 530 supported on shaft 520 towards the distal end thereof. Shaft 520 may define a flexible configuration to facilitate positioning within the colon "C" (FIG. 5B). End effector 530 includes a pair of longitudinally-spaced balloons 542, 544 defining a exposed portion 522 of shaft 520 therebetween.

Instrument 500 further includes a first fluid tube 550 configured to connect to an inflation source 560. First fluid tube 550 extends into handle 510 and through shaft 520, ultimately coupling to balloons 542, 544 such that inflation fluid, e.g., air, may be delivered to and removed from balloons 542, 544 to inflate and deflate balloons 542, 544.

Further, a rocker switch 512, or other suitable activation member(s), disposed on handle 510 and operably coupled to inflation source 560 and/or fluid tube 550 is provided to enable the selective inflation and deflation of balloons 542, 544. More specifically, when a first portion 513a of rocker switch 512 is activated, pressure is supplied to pump fluid through first fluid tube 550 and into balloons 542, 544 to inflate balloons 542, 544. On the other hand, when a second portion 513b of rocker switch 512 is activated, suction is applied to withdraw fluid from balloons 542, 544 through fluid tube 550 to deflate balloons 542, 544. Alternatively, balloons 542, 544 may be independently inflatable and deflatable, e.g., via providing separate activation buttons.

Exposed portion 522 of shaft 520 includes a plurality of ports 524 defined therethrough. Ports 524 are disposed at various radial and/or longitudinal positions along exposed portion 522 of shaft 520 and are each fluidly coupled with a second fluid tube 570 extending proximally through shaft 520, handle 510, and proximally therefrom. Second fluid tube 570 ultimate couples to an external treatment source 580. Treatment source 580 is configured to pump heated fluid "HF," e.g., steam, hot water, etc., through second fluid tube 570 and out ports 524, into the area disposed between balloons 542, 544. An activation button 514 disposed on handle 510 is operably coupled to second fluid tube 570 and/or treatment source 580 to enable the selective pumping of heated fluid "HF" through second fluid tube 570 and ports 524.

In use, shaft 520 of instrument 500, led by end effector 530, is inserted into the colon "C" such that end effector 530 is positioned adjacent the diseased area "A" of the colon "C" to be treated. Shaft 520 may be inserted through the anus and navigated through the colon "C" to the diseased area "A," as illustrated, although other approaches are also contemplated. With end effector 530 positioned as desired, first portion 513a of rocker switch 512 may be activated to supply inflation fluid from the inflation source 560 through fluid tube 550 to balloons 542, 544 to inflate balloons 542, 544. Balloons 542, 544 are sufficiently inflated so as to sealingly engage the inner wall of the colon "C" adjacent each balloon 542, 544. This sealing engagement of balloons 542, 544 with the inner wall of the colon "C" seals off at least a portion of the diseased area "A" of the colon "C" with exposed portion 522 of shaft 520 extending through this sealed, diseased area "A."

Thereafter, activation button 514 may be actuated to initiate the supply of the heated fluid "HF" from the treatment source 580, through second fluid tube 570, out ports 524, and into the sealed diseased area "A" disposed between balloons 542, 544. The heated fluid "HF" is pumped into the diseased area "A" so as to at least partially fill the diseased area "A" and contact the layer of inflamed, diseased tissue defining the diseased area "A" of the colon "C." Balloons 542, 544, which sealingly enclose the diseased area "A" or portion thereof, retain the heated fluid "HF" within the diseased area "A" or portion thereof, thus inhibiting damage to surrounding tissue. The heated fluid "HF" may be heated to or above about 43° C. or, in some embodiments, to or above about 60° C. such that the heated fluid "HF" is capable of thermally treating the layer of inflamed, diseased tissue, e.g., via burning, charring, ablating, coagulating, and/or desiccating, the inflamed layer of tissue.

Once sufficient thermal treatment of the inflamed, diseased layer of tissue has been achieved, treatment source 580 may be transitioned from a pressure mode to a suction mode to withdraw the heated fluid "HF" from the diseased area "A." Further, similarly as detailed above, a cooling fluid source (not shown, similar to cooling fluid source 350 (FIG. 3)), may be activated to pump cooling fluid "CF" (FIG. 3) into the diseased area "A" to cool the treated tissue. The temperature and duration of the application of the heated fluid "HF" and/or cooling fluid "CF" (FIG. 3) can be controlled such that the thermal treatment extends sufficiently deep into the diseased tissue defining the diseased area "A" so as to adequately treat the tissue, while being sufficiently contained so as to inhibit damage to surrounding tissue and critical structures.

Instrument 500 may subsequently be used to treat other diseased area(s) of the colon "C" in either an incremental fashion or a continuous fashion. More specifically, with respect to use in an incremental fashion, after treatment as detailed above, balloons 542, 544 may be deflated, e.g., via activating second portion 513b of rocker switch 512, allowing end effector 530 to be repositioned adjacent another diseased area to be treated. Thereafter, balloons 542, 544 may be re-inflated and subsequent treatment of the other diseased area(s) may be accomplished in a similar fashion as detailed above, e.g., using heated fluid "HF." With respect to use in the continuous fashion, instrument 500, with balloons 542, 544 maintained in the inflated state, may be pulled through the colon "C" such that the sealed area between balloons 542, 544, is moved along the colon "C." As the sealed area is moved along the colon "C," the heated fluid "HF" may be supplied through ports 524 to the sealed area, as detailed above, to continuously thermally treat tissue as the instrument 500 is moved through the colon "C."

Figure 6A:
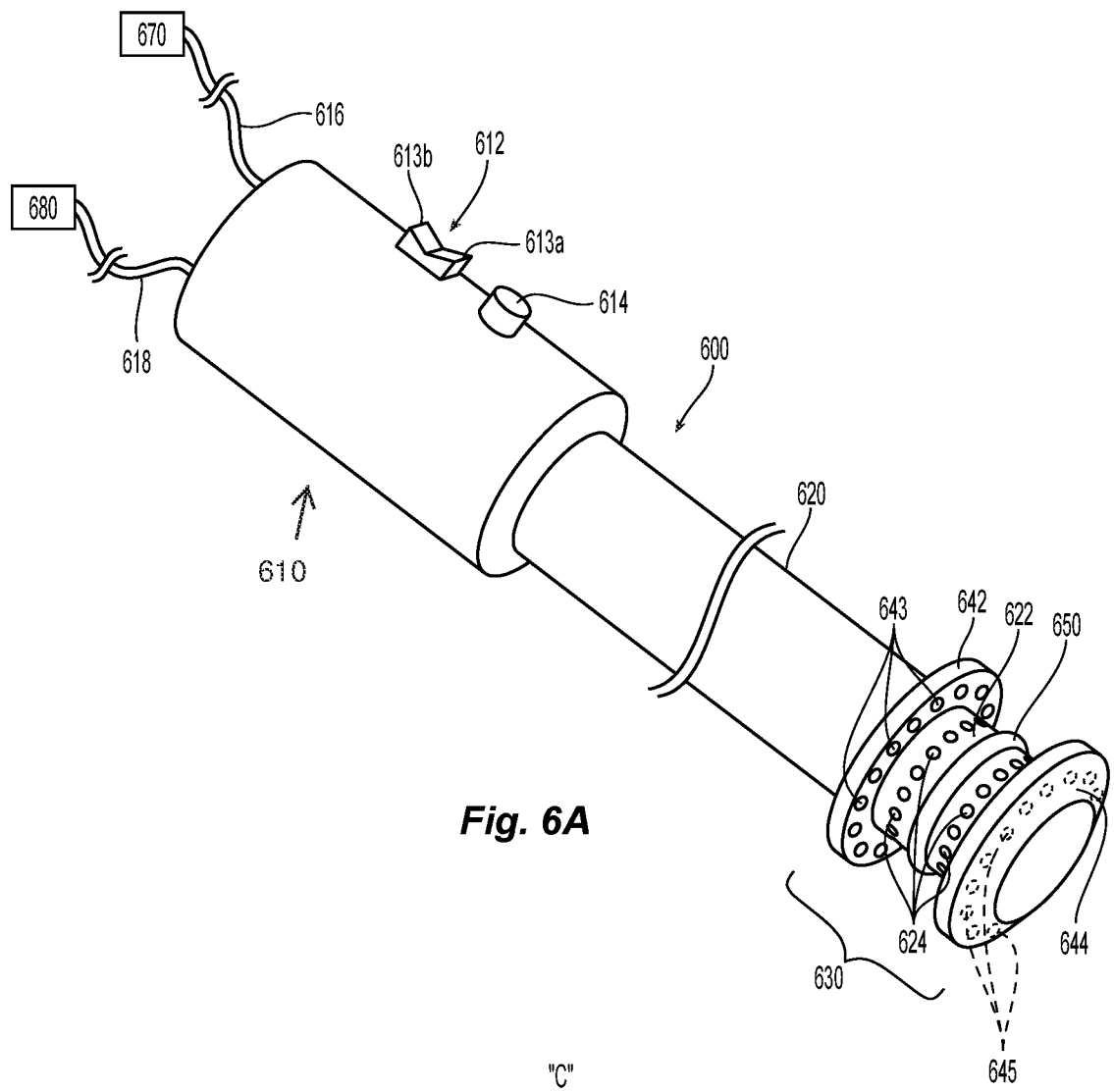
FIG. 6A is a perspective view of another device provided in accordance with the present disclosure configured for use in treating a diseased portion of the colon.
Figure 6B:
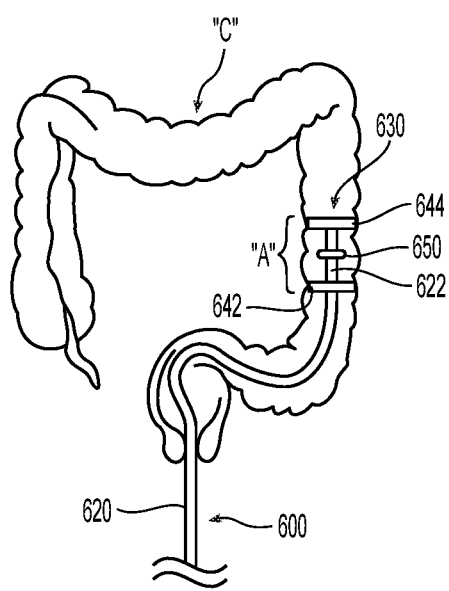
FIG. 6B is a schematic illustration of the device of FIG. 6A shown in use treating a diseased portion of the colon.

Turning to FIGS. 6A and 6B, another instrument 600 provided in accordance with the present disclosure and configured for use in treating IBD's is shown generally including a handle 610, a shaft 620 extending distally from handle 610, and an end effector 630 supported on shaft 620 towards the distal end thereof. Handle 610 includes a rocker switch 612 and activation button 614 disposed thereon, an electrical cable 616 coupled thereto and extending therefrom, and a fluid tube 618 coupled thereto and extending therefrom. Shaft 620 may define a flexible configuration to facilitate positioning within the colon "C" (FIG. 6B).

End effector 630, as mentioned above, is disposed about shaft 620 towards the distal end thereof. End effector 630 includes a pair of longitudinally-spaced disc members 642, 644 disposed about shaft 620 so as to define an exposed portion 622 of shaft 620 therebetween. A ring electrode 650 of end effector 630 is disposed about exposed portion 622 of shaft 620 between disc members 642, 644. Exposed portion 622 of shaft 620 defines a plurality of ports 624 disposed at various radial and/or longitudinal positions along exposed portion 622 of shaft 620.

Disc members 642, 644 are configured to enable positioning within the colon "C" in sealing engagement therewith. More specifically, disc members 642, 644 may be configured to enable such sealing engagement based upon the dimensions thereof and/or may include resiliently flexible portions, inflatable portions, etc. to facilitate formation of a seal within the colon "C" to seal off a diseased area "A" to be treated between disc members 642, 644. Disc members 642, 644 further include a plurality of ports 643, 645 disposed on longitudinally-opposed faces thereof and arranged radially about shaft 620.

Ports 643, 645 of disc members 642, 644, respectively, and ports 624 of exposed portion 622 of shaft 620 are fluidly coupled with fluid tube 618, which extends distally through handle 610 and shaft 620. Fluid tube 618 is ultimately configured to couple to a fluid source 670 for pumping an electrically-conductive fluid through fluid tube 618 and some or all of ports 624, 643, 645. Fluid source 670 may further be configured for suctioning the electrically-conductive fluid through some or all of ports 624, 643, 645 and fluid tube 618. Fluid tube 618 may include separate inlet and outlet lumens (not shown) for the inflow and outflow of the electrically-conductive fluid or may be configured to permit both the inflow and outflow of the electrically-conductive fluid through a common lumen. Further, some of the ports, e.g., ports 624, may be configured for inflow to deliver the electrically-conductive fluid to the diseased area "A," while other ports, e.g., ports 643, 645, may be configured for outflow to withdraw the electrically-conductive fluid from the diseased area "A." However, the reverse configuration or other suitable configurations are also contemplated.

Rocker switch 612 is disposed on handle 610, operably coupled to the fluid source 670 and/or fluid tube 618, and configured to enable the selective pumping and suctioning of the electrically-conductive fluid through fluid tube 618 and ports 624, 643, 645. More specifically, when a first portion 613a of rocker switch 612 is activated, the electrically-conductive fluid is pumped through fluid tube 618 and out some or all of ports 624, 643, 645. On the other hand, when a second portion 613b of rocker switch 612 is activated, suction is applied through fluid tube 618 to suction the electrically-conductive fluid through some or all of ports 624, 643, 645 and fluid tube 618. The electrically-conductive fluid may be any suitable biocompatible fluid capable of conducting electrical energy therethrough such as, for example, a conductive gel, isotonic saline, argon plasma, etc.

Ring electrode 650, as mentioned above, is disposed about exposed portion 622 of shaft 620 between disc members 642, 644. Ring electrode 650 is electrically coupled with electrical cable 616, e.g., via one or more electrical leads (not shown) extending through shaft 620 and handle 610. Electrical cable 616, in turn, is configured to couple to an electrosurgical generator 680 configured to supply electrosurgical energy to the ring electrodes 650. Generator 680 may be configured to supply monopolar energy to ring electrode 650, with the energy being returned to generator 680 via a remote return pad (not shown) placed on the patient. However, bipolar energy configurations are also contemplated. Activation button 614 is disposed on handle 610 and operably coupled between generator 680 and ring electrode 650 to enable the selective supply of energy to ring electrode 650.

In use, shaft 620 of instrument 600, led by end effector 630, is inserted into the colon "C" such that end effector 630 is positioned adjacent the diseased area "A" of the colon "C" to be treated. Shaft 620 may be inserted through the anus and navigated through the colon "C" to the diseased area "A," as illustrated, although other approaches are also contemplated. With end effector 630 positioned in this manner, disc members 642, 644 are disposed on either side of the diseased area "A" (or a portion thereof) sealingly enclosing the diseased area "A."

Once this position has been achieved, first portion 613a of rocker switch 612 may be activated to pump the electrically-conductive fluid through fluid tube 618 and out some or all of ports 624, 643, 645 into the diseased area "A" to at least partially fill the diseased area "A."

After the electrically-conductive fluid has been introduced, or concurrently therewith, activation button 614 may be actuated to initiate the supply of energy to ring electrode 650. Upon energization of the ring electrode 650, the electrically-conductive fluid facilitates the conduction of energy therethrough and to the layer of inflamed, diseased tissue defining the diseased area "A" of the colon "C" for electrosurgically treating the layer of inflamed, diseased tissue, e.g., via burning, charring, ablating, coagulating, and/or desiccating the inflamed layer of tissue.

Once tissue has been treated, or intermittently during tissue treatment, second portion 613b of rocker switch 612 may be activated to withdraw the electrically-conductive fluid through fluid tube 618, allowing for subsequent introduction of additional electrically-conductive fluid. Alternatively, instead of a rocker switch 612, instrument 600 may be provided with an activation switch (not shown) that concurrently provides both pumping and suctioning of the electrically-conductive fluid. Such a configuration may be particular advantageous with respect to the use of argon plasma as the electrically-conductive fluid, wherein the suctioning defines an exhaust path, while the pumping concurrently provides additional electrically-conductive fluid to replace the exhausted fluid.

Instrument 600 may subsequently be used to treat other diseased area(s) of the colon "C" in either an incremental fashion or a continuous fashion, similarly as detailed above with respect to instrument 500 (FIGS. 5A and 5B).

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. A method of treating bowel diseases, comprising:
   sealing off a portion of a patient's colon between a proximal plug and a distal plug;
   introducing an electrically-conductive fluid into the sealed off portion of the patient's colon through a probe defining a lumen therein, a distal end of the probe terminating proximal to the distal plug in the sealed off portion of the patient's colon;
   advancing an electrode through the lumen, wherein the electrode is advanced through the distal end of the probe into the sealed off portion of the patient's colon to position the electrode between the distal-most end of the probe and the distal plug; and
   energizing the electrode disposed within the sealed off portion of the patient's colon such that energy is conducted through the electrically-conductive fluid and tissue of the portion of the patient's colon in contact with the electrically-conductive fluid to treat tissue of the portion of the patient's colon in contact with the electrically-conductive fluid.

2. The method according to claim 1, wherein the electrically-conductive fluid is an electrically-conductive gel, argon plasma, or isotonic saline.

3. The method according to claim 1, wherein the electrically-conductive fluid includes at least one medicament therein to facilitate healing of treated tissue.

4. The method according to claim 1, wherein sealing off the portion of the patient's colon includes clamping or plugging at least one end of the portion of the patient's colon.

5. The method according to claim 4, further including inserting the electrode through a clamped or plugged end of the portion of the patient's colon and into the portion of the patient's colon prior to energizing the electrode.

6. The method according to claim 1, wherein sealing off the portion of the patient's colon includes:

introducing an end effector into the patient's colon; and engaging first and second sealing members of the end effector with respective ends of the portion of the patient's colon.

7. The method according to claim 6, wherein introducing the electrically-conductive fluid includes pumping the electrically-conductive fluid through a port of the end effector disposed between the first and second sealing members.

8. The method according to claim 6, wherein energizing the electrode includes energizing an electrode of the end effector disposed between the first and second sealing members.

9. The method according to claim 1, wherein energizing the electrode includes applying monopolar energy to the electrode.

10. The method according to claim 1, wherein the distal end of the probe is unconnected with the distal plug.

11. A method of treating bowel diseases, comprising:

sealing off a portion of a patient's colon by positioning a first plug at a first portion of the patient's colon and a second plug at a second portion of the patient's colon to create a sealed off portion between the first plug and the second plug;

passing a probe through the first plug such that a distal end of the probe is positioned between the first plug and the second plug;

introducing an electrically-conductive fluid into the sealed off portion of the patient's colon through the distal end of the probe;

advancing an electrode through the distal end of the probe to position the electrode in the sealed off portion of the patient's colon, wherein the electrode is advanced through the distal end of the probe to position the electrode between the distal-most end of the probe and the distal plug; and energizing the electrode positioned within the sealed off portion of the patient's colon such that energy is conducted through the electrically-conductive fluid and tissue of the portion of the patient's colon in contact with the electrically-conductive fluid to treat tissue of the portion of the patient's colon in contact with the electrically-conductive fluid.

* * * * *